US005528774A

United States Patent [19]
Sanders

[11] Patent Number: 5,528,774
[45] Date of Patent: Jun. 25, 1996

[54] EARMUFF ASSEMBLY

[76] Inventor: Linda I. Sanders, 340 Ellis Way, Golden, Colo. 80401

[21] Appl. No.: 149,658

[22] Filed: Nov. 5, 1993

[51] Int. Cl.[6] .................................................. A42B 3/16
[52] U.S. Cl. .............................. 2/209; 2/171; 2/DIG. 11
[58] Field of Search ................................. 2/2, 171, 208, 2/209, 423, DIG. 11; 128/857, 859, 864, 866, 867, 868; D2/624, 627, 635, 894; D29/112

[56] References Cited

U.S. PATENT DOCUMENTS

| | | | |
|---|---|---|---|
| D. 101,297 | 9/1936 | Appelbaum et al. | D2/627 |
| 1,768,068 | 6/1930 | Jauss . | |
| 2,456,167 | 12/1948 | Arkus | 2/209 |
| 2,609,544 | 9/1952 | Berg | 2/209 |
| 2,693,599 | 11/1954 | Berg | 2/209 |
| 4,633,530 | 1/1987 | Satterfield | 2/209 |
| 5,038,412 | 8/1991 | Cionni . | |
| 5,231,704 | 8/1933 | Hildenbrand | 2/209 |

*Primary Examiner*—Diana Biefeld

[57] ABSTRACT

An earmuff assembly is adapted to be secured to a wearer's head in order to cover the wearer's ears. The earmuff assembly comprises a pair of earmuff elements, a band member and a joining means. Each of the earmuff elements has a pair of spaced-apart sleeve structures disposed thereon. The band member has opposite ends and includes a pair of strap portions. A first one of strap portions is slidably received in a first one of the sleeve structures of each earmuff element and a second one of the strap portions is slidably received in a second one of the sleeve structures of each earmuff element so that the earmuff element may be selectably positioned along the band member between the strap portions. The joining means interconnects the opposite ends of the band member so that the band member may be placed around and retained by the head of the wearer with the earmuff elements oriented to cover the ears. Another embodiment includes a pair of elastic strap elements which are connected to each other at respective first and second ends to form a pair of coupled ends and a continuous band member. A respective one of a matable pair of fastening devices is connected to a respective one of the coupled ends. Yet another embodiment includes an elastic continous band member having a pair of loop portions that are interlinked to each other.

27 Claims, 4 Drawing Sheets

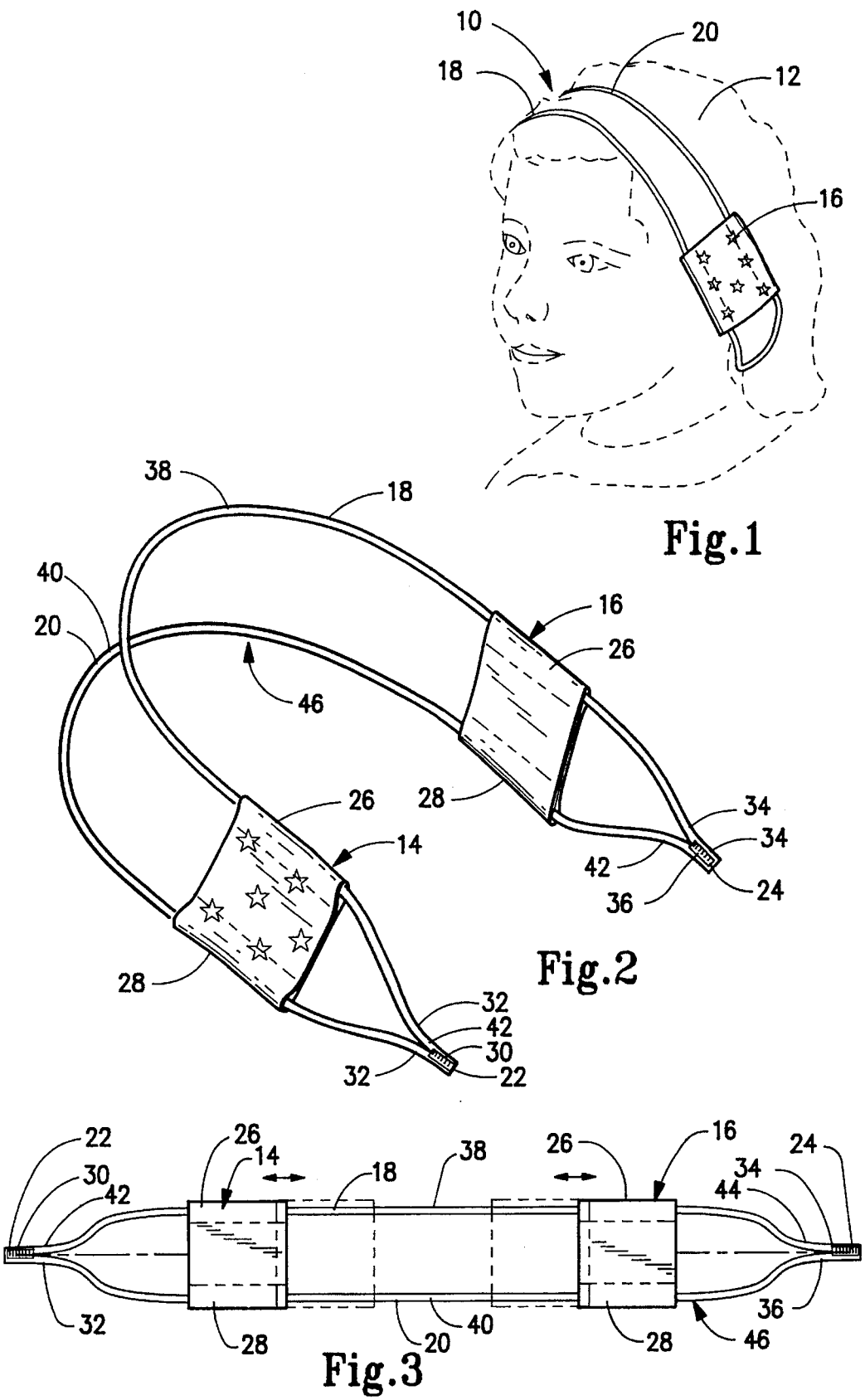

5,528,774

EARMUFF ASSEMBLY

FIELD OF THE INVENTION

The present invention relates to ear protection. More particularly, the present invention concerns an earmuff assembly which is adapted to be secured to a wearer's head in order to cover the wearer's ears to protect them from adverse weather conditions.

BACKGROUND OF THE INVENTION

The need for persons to don protective clothing during times of exposure to cold temperatures has always been known. Indeed, various garments have been specially developed to protect different parts of the body; among these are various hats, caps and other headgear adapted to protect a wearer's ears. For example, some hats and caps include flap portions that can be either extended downwardly over the ears when worn on the head or retracted away from the ears, if desired. Stocking-type caps are often sized so that they may be rolled into a thick peripheral margin away from the ears but unrolled over the ears when extra ear protection is sought. Some stocking-type caps are constructed to encase the entire head, including the ears, leaving only small openings for the eyes, nose and mouth.

In addition to these examples of headwear, specifically designed independent protectors for the ears, are known and are commonly referred to as earmuffs, and it is to this type of ear protector that the present invention is concerned. Typically, earmuffs comprise a pair of earmuff elements each in the form of a large, thick, insulated disk sized to cover the ear. These earmuff elements are rather stiff constructs, and they are usually interconnected by an arcuate strip of metal or plastic that is stiff, yet resilient enough so that the earmuff elements may be positioned over the ears or held in position with the spring-like action of the band member which arches over and is supported by the top of the wearer's head. While being fairly functional, thee earmuffs are somewhat awkward and uncomfortable to wear. Moreover, they lack fashion appeal and, indeed, disrupt hair styling due to the compression of the hair by the stiff arcuate band and by the earmuff elements. For these reasons, many people avoid wearing protective earmuffs.

Other types of earmuffs are known and are described in various published patents. One such structure is shown in U.S. Pat. No. 2,609,544 issued Sep. 9, 1952 to Berg wherein an earmuff assembly includes a securing band and a pair of earmuffs which are slidably mounted on the band so that they may be adjusted upwardly or downwardly along the band to fit over the ears of the wearer. One end of the band is connected to a buckle and the other end of the band is threaded therethrough for adjusting the length and relative tightness of the band about the wearer's head. Each earmuff includes a rigid ring having a pair of opposite holes through which the band extends. An earmuff covering is formed of two different types of fabric such as an inner layer of wood or cotton felt and an outer layer of nap-covered fabric or natural lamb's wool.

U.S. Pat. No. 2,693,599 issued Nov. 9, 1954 to Berg, discloses an earmuff assembly comprising an elastic band and a pair of earmuffs slidably mounted on the elastic band. The ends of the band are secured together to form an endless band which must be stretched to surround the wearer's head. Each of the earmuffs comprise an outer circular conical shell of smooth, shiny sheet plastic consisting of a disk having a radial slit from its periphery to its center. The edges of the slit are overlapped and connected together with a tubular rivet thereby forming a shallow cone. Each of the shells has a pair of opposed elongated holes adjacent the outer edges and extending parallel to the periphery for receiving the band. Each of the shells has a lining of native lambs' wool with a leather backing.

U.S. Pat. No. 2,456,167 issued Dec. 14, 1948 to Arkus describes an earmuff assembly which can also be used as a head ornament. The earmuff assembly comprises an elongated, limp tape and a pair of earmuffs. Each earmuff includes a flat outer layer of material and a flat inner layer of material. The tape is threaded through a passageway provided in association with each earmuff so that it is slidable on the tape. The connection between the tape and the earmuffs is slidable in order to allow movement of both earmuffs along the tape so that the earmuffs can be moved from a position covering the ears to any other position along the tape. One other position might be located above the ears, at which the earmuffs form attractive decorations.

Each of the prior art earmuff assemblies disclose only a single band which encircles the wearer's head. A single band is suitable for each of the Berg patents because the earmuffs are fabricated from a rigid or substantially rigid material. In the Arkus patent, where the earmuffs are fabricated from a fabric material, wind can cause the earmuffs to be blown away from contact with the wearer's ears. Also, earmuff assemblies that are fabricated from a rigid material or a substantially rigid material are generally heavy to carry, uncomfortable to wear and rather bulky for storage when not in use.

A need exists to provide an earmuff assembly that is comfortable, compact, and lightweight. There is also a need to provide an earmuff assembly having such characteristics that cannot be blown away from the wearer's ears in windy conditions. Further, there remains a need for fashionable earmuffs that cause reduced damage to a hair style. The present invention is directed to such an invention.

SUMMARY OF INVENTION

It is an object of the present invention to provide a new and useful earmuff assembly that is comfortable to wear, compact for storage and lightweight.

It is a further object of the present invention to provide an earmuff assembly having earmuff elements that cannot be easily blown away from the wearer's ears during windy conditions.

It is another object of the present invention to provide an earmuff assembly that can be adjusted for security and tightness around numerous sizes of heads.

It is yet a further object of the present invention to provide an earmuff assembly having earmuff elements that can be adjusted into a myriad of positions to accommodate various ear positions of various sized heads.

It is still another object of the present invention to provide an earmuff assembly that is fashionable to wear.

Yet another object of the present invention is to provide an earmuff assembly that can be worn with limited effect on a hair style.

According to the present invention, an earmuff assembly is described which is adapted to be secured to a wearer's head in order to cover the wearer's ears. In its broadest form, the earmuff assembly comprises a pair of earmuff elements and a band member. Each of the earmuff elements has a pair of spaced-apart sleeve structures which are disposed thereon, and the band member includes a pair of strap portions that slidably extend through the respective sleeve structures to retain the earmuff elements thereon. Opposite ends of the band member may be joined to secure the band member around a wearer's head with the earmuff elements covering the ears.

The pair of earmuff elements are sized to cover the wearer's ears and are preferably fabricated from a pliable material such as fabric, leather, animal fur and imitation animal fur. Each of the earmuff elements can be constructed in a rectangular shape out of a pair of sections of pliable material which are sized to be superimposed over and connected to each other to form the first and second sleeve structures. Naturally, the earmuff elements can take shapes other than rectangular, as desired. In any event it is preferable that one of the sections of pliable material is decorative so as to increase the fashion appeal of the earmuff assembly. The first and second sleeve structures of each earmuff element are disposed substantially parallel to one another. Each of the sleeve structures can be a tubular member or, in the alternative, each of the sleeve structures includes a plurality of eyelets.

The pair of strap portions which form the band member allow the earmuff elements to be selectively positioned along the band member between the strap portions to adjust to the location of the wearer's ears. It is preferable that the band member is fabricated from an elastic material and be of reduced size so as to be unobtrusive and exert minimal damage to a hair style. Alternatively, the band member may have only portions thereof formed of elastic material sufficient to allow the earmuff assembly to be slipped onto and off of the wearer's head. The band member may be constructed of flexible, non-elastic pieces provided that the opposite ends are securable to one another by adjustable connector or by an elastic piece.

In one embodiment of the invention, the band member is formed as a continuous elastic loop that is arranged so that opposite loop portions that define the ends of the band member are interlinked or coupled with one another. Where the ends of the band member are separable, cooperative connectors are used to releasably interconnect the opposite ends of the band member so that the band member may be placed around and be retained by the head of the wearer with the earmuff elements oriented to cover the ears. Examples of the cooperative connectors include a matable pair of fastener elements, each of which is adapted to connect to a respective one of the opposite ends, a hook and loop fastening stirps, a button and loop fastener, a snap fastener, and a button and hole fastener.

These and other objects of the present invention will become more readily appreciated and understood from a consideration of the following detailed description of the exemplary embodiments of the present invention when taken together with the accompanying drawings, in which:

BRIEF DESCRIPTION OF DRAWINGS

FIG. 1 is a perspective view of a first exemplary embodiment of an earmuff assembly of the present invention in a fastened state and secured to a wearer's head in order to cover the wearer's ears;

FIG. 2 is a perspective view of the earmuff assembly of FIG. 1 in an unfastened state;

FIG. 3 is a rear view in elevation of the earmuff assembly of FIGS. 1 and 2 showing a pair of earmuff elements which are slidable into various positions;

DETAILED DESCRIPTION OF THE EXEMPLARY EMBODIMENTS

Figure 4:
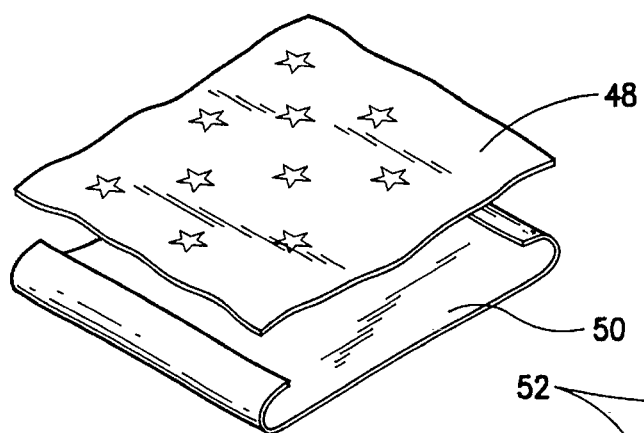
FIG. 4 is an exploded perspective view of an earmuff element comprising a pair of sections of pliable material.

The present invention generally concerns an earmuff assembly which is adapted to be secured to a wearer's head in order to cover the wearer's ears. Several exemplary embodiments of the present invention have been selected as examples for the detailed description. However, it should be understood by one of ordinary skill in the art that other embodiments of the present invention can be made without departing from the inventive concepts contained herein.

The first embodiment of an earmuff assembly 10 of the present invention is generally introduced in FIGS. 1–3. Earmuff assembly 10 is adapted to a wearer's head 12 in order to cover the wearer's ears and comprises a pair of earmuff elements 14, 16, a pair of elastic strap elements 18, 20 and a matable pair of fastening elements 22, 24. Each earmuff element 14, 16 has a pair of spaced-apart sleeve structures 26, 28 disposed thereon in a substantially parallel relationship. The pair of earmuff elements 14, 16 are sized to cover the wearer's ears and are fabricated from a pliable material shaped substantially rectangularly. Of course, shapes other than rectangular may be used without departing from the scope of this invention.

Each of elastic strap elements 18, 20 has a first end 30, 32 and an opposite second end 34, 36 and a central portion 38, 40. Central portion 38 of strap element 18 extends between first end 30 and second end 34 and central portion 40 of strap element 20 extends between first end 32 and second end 36. A first one of central portions 38, 40 is slidably received in a first one of said sleeve structures 26 of each earmuff element 14, 16 and a second one of central portions 38, 40 is slidably received in a second one of said sleeve structures 28 of each earmuff element 14, 16 so that earmuff elements 14, 16 may be slidably positioned along said pair of strap elements 18, 20 to a selected location as shown in FIG. 3. Respective ones of first ends 30, 32 and second ends 34, 36 are connected to each other forming a pair of coupled ends 42, 44 and thus forming a continuous band member 46.

By way of example only, the pair of fastening elementss 22, 24 are shown as conventional hook and loop fasteners. A respective one of each fastening elements 22, 24 is connected to a respective one of said coupled ends 42, 44 so that coupled ends 42, 44 may be releasably connected to each other. Now, continuous band member 46 may be placed around and be elastically retained by the head 12 of the wearer with earmuff elements 14, 16 oriented to cover the ears.

Figure 5:
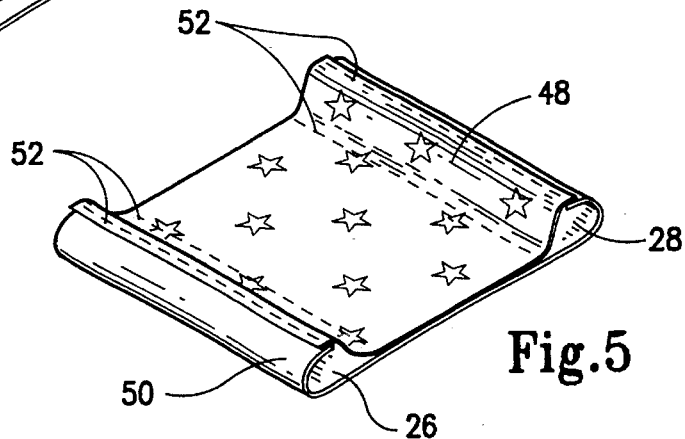
FIG. 5 is a perspective view of the earmuff element of FIG. 4 showing the pair of sections of pliable material connected to each other to form a pair of sleeve structures.

As best shown in FIGS. 4 and 5, each of earmuff elements 14, 16 includes a pair of sections of pliable material 48, 50. Sections of pliable material 48, 50 are sized to be superimposed over and connected to each other by sewing a series of seams 52 thereacross to form first and second sleeve structures 26, 28. Although not by way of limitation, each first and second sleeve structures 26, 28 is a tubular member. It is preferable that one of sections of pliable material 48, 50 is decorative as reflected by a select pattern of a star design as shown in FIGS. 1, 2 and 4. Having an outer decorative section of pliable material provides an attractive, fashionable earmuff assembly 10.

Figure 6:
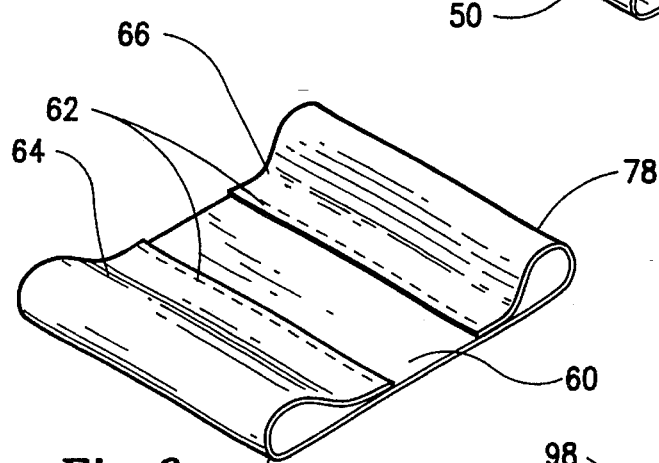
FIG. 6 is a first alternative embodiment of the earmuff element shown in FIGS. 4 and 5 forming a pair of sleeve structures.
Figure 7:
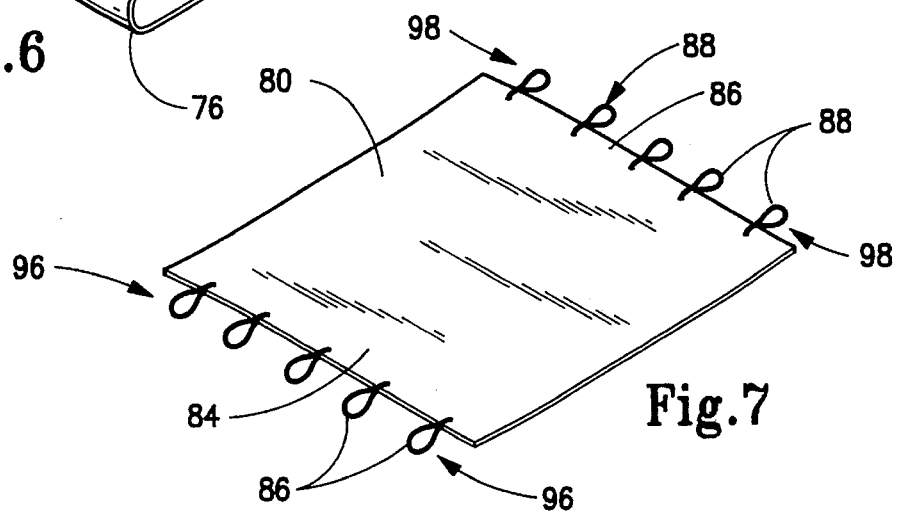
FIG. 7 is a second alternative embodiment of the earmuff element shown in FIGS. 4 and 5.

Two other embodiments of earmuff elements are depicted in FIGS. 6 and 7. In FIG. 6, a single section of pliable material 60 is folded along opposite lateral edges 64, 66 and sewn therealong by seams 62 to form first and second sleeve structures 76, 78. In FIG. 7, a single section of pliable material 80 has an array of eyelets 88 connected along opposite lateral edges 84, 86 to form an alternative first and second sleeve structures 96, 98.

Figure 8:
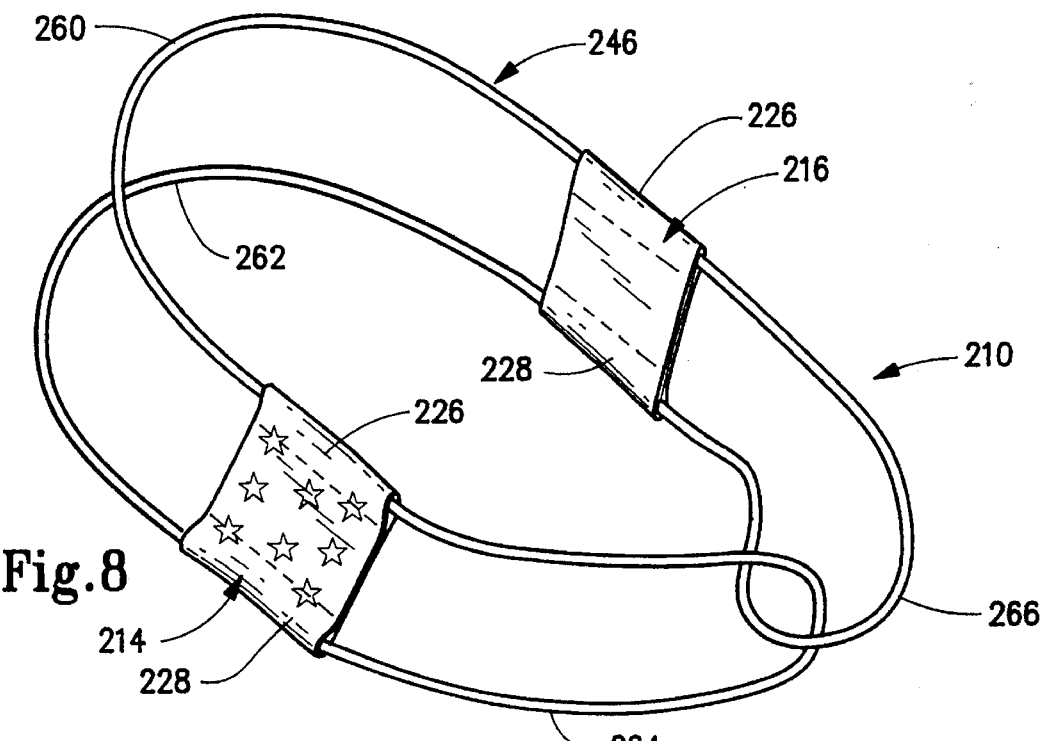
FIG. 8 is a perspective view of a second exemplary embodiment of an earmuff assembly of the present invention showing interlinked or coupled loop portions of a continuous band member.

A second exemplary embodiment of an earmuff assembly is illustrated in FIG. 8. Here, earmuff assembly 210 comprises a pair of earmuff elements 214, 216 and an elastic continuous band member 246. Continuous band member 246 is defined by a pair of strap portions 260, 262 interconnected by a pair of loop portions 264, 266 that define the ends of band member 246. The pair of strap portions 260, 262 extend through and between earmuff elements 214, 216 and the pair of loop portions 264, 266 extend opposite one another outwardly from respective ones of said earmuff elements 214, 216. A first one of said strap portions 260, 262 is slidably received in a first one of sleeve structures 226, 228 of each earmuff element 214, 216 and a second one of said strap portions 260, 262 is slidably received in a second one of said sleeve structures 226, 228 of each earmuff element 214, 216 whereby earmuff elements 214, 216 may be selectively positioned along said pair of strap portions 260, 262. Loop portions 264, 266 are interlinked or coupled to each other to provide a joining means so that said continuous band 246 may be placed around and be retained by the head of the wearer with said earmuff elements 214, 216 oriented to cover the ears. It is preferable that continuous band member is fabricated from an elastic material.

Figure 9:
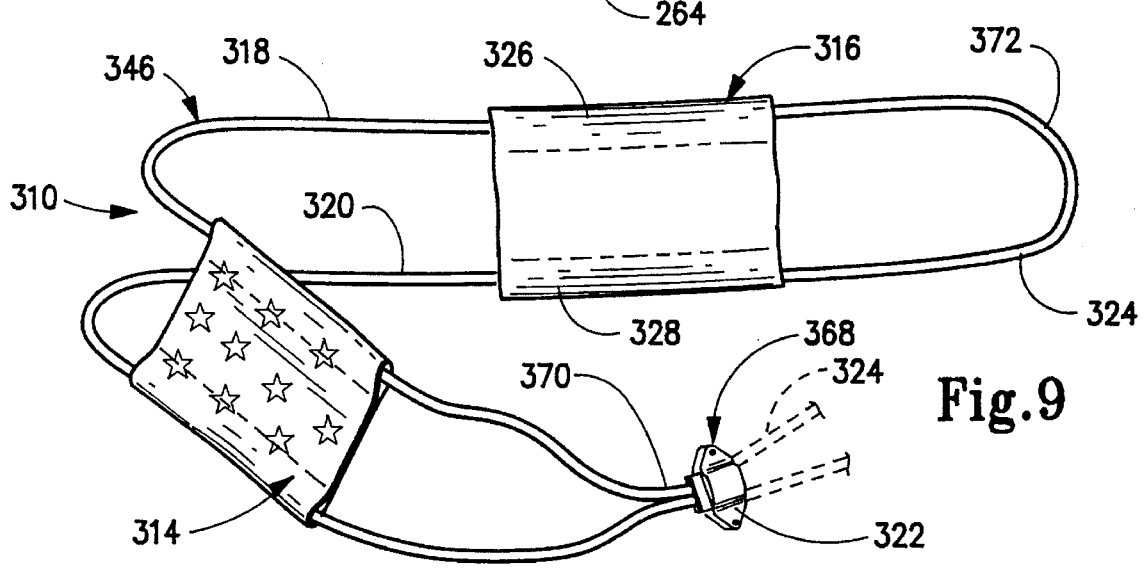
FIG. 9 is a perspective view of a third exemplary embodiment of an earmuff assembly of the present invention showing a button and loop fastener element.

A third exemplary embodiment of an earmuff assembly of the present invention is illustrated in FIG. 9. Here, earmuff assembly 310 comprises a pair of earmuff elements 314, 316, a band member 346 and a joining means 368. The pair of earmuff elements 314, 316 each have a pair of spaced-apart sleeve structures 326, 328 disposed thereon. Band member 346 has opposite ends 370, 372 and includes a pair of strap portions 318, 320. A first one of strap portions 318, 320 is slidably received in a first one of sleeve structures 326, 328 of each earmuff element 314, 316 and a second one of strap portions 318, 320 is slidably received in a second one of sleeve structures 326, 328 of each earmuff element 314, 316 whereby earmuff elements 314, 316 may be selectively positioned along said band member 346 between said strap portions 318, 320.

The opposite ends 370, 372 of said band member 346 may be interconnected or joined so that band member 346 may be placed around and be retained by the head 12 of the wearer with said earmuff elements 314, 316 oriented to cover the ears. In this embodiment, the joining means is provided by loop portion 324 of band member 346 and a cooperating fastener element 322. Fastener element 322 is sized to engage loop portion 324 in a conventional button and loop manner.

Figure 10:
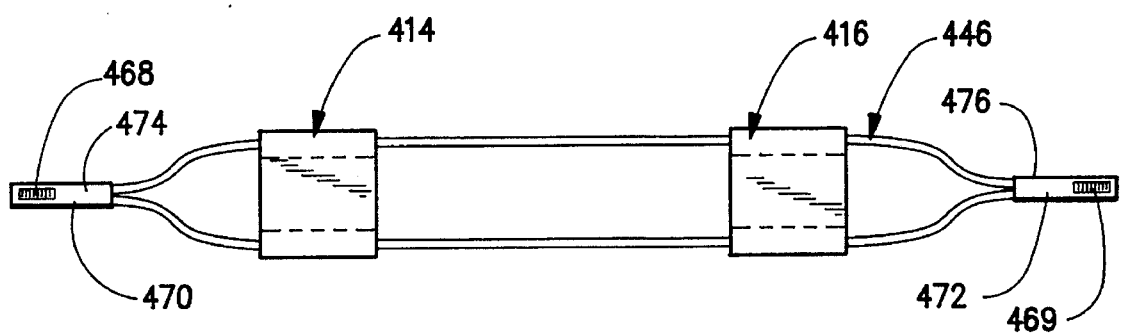
FIG. 10 is a perspective view of a fourth exemplary embodiment of an earmuff assembly of the present invention showing a band member having appropriate end portions fabricated from an elastic material.

A fourth exemplary embodiment of an earmuff assembly of the present invention is depicted in FIG. 10. In this embodiment, earmuff assembly 410 comprises a pair of earmuff elements 414, 416, a band member 446 and a joining means formed by cooperating hook and loop fastening strips 468, 469 for interconnecting opposite ends 470, 472. Opposite ends 470, 472 each include an elastic web 474, 476, respectively, which enables the wearer to adjust the tension of earmuff assembly 410 onto the wearer's head, particularly when band member 446 is fabricated from a material that is relatively non-elastic.

For any of the exemplary embodiments of the earmuff assembly of the present invention, it is preferable that the pliable material employed to construct the earmuff elements is fabric, leather, animal fur or imitation animal fur. Although other materials could be selected, it would be advantageous that this material exhibits good insulation qualities.

Figure 11:
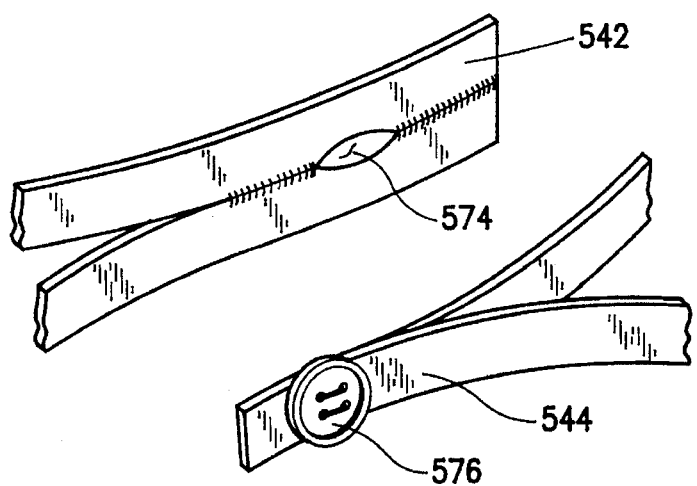
FIG. 11 is a perspective view of respective opposite ends of the band member showing a button and hole fastener element.
Figure 12:
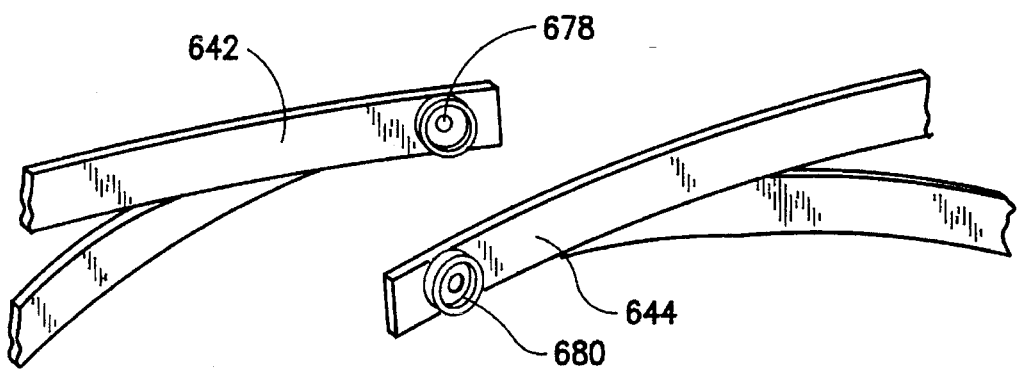
FIG. 12 is a perspective of opposite ends of the band member showing a snap fastener element.
Figure 13:
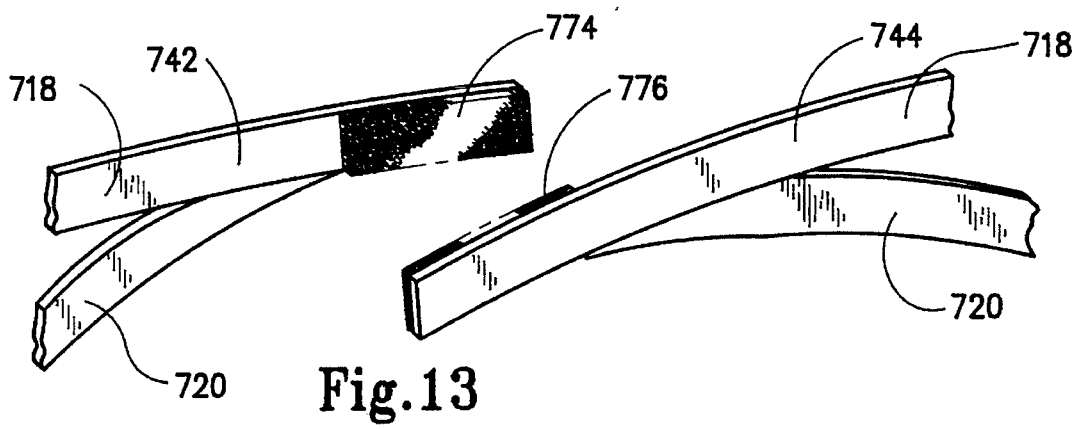
FIG. 13 is a perspective view of respective opposite ends of the band member employing non-elastic strap portions and adjustable cooperating hook and loop fastening strips.

One of ordinary skill in the art would appreciate that other alternative embodiments of fastener elements are readily available in the marketplace and can be easily adapted for use with the earmuff assembly of the present invention. Three such examples of alternative embodiments of fastener elements are shown in FIGS. 11–13. In FIG. 11, coupled end 542 includes a button hole 574 and coupled end 544 includes a conventional button 576 to form a conventional button and hole fastener. In FIG. 12, coupled end 642 includes a female snap 578 and coupled end 644 includes a male snap 580 to form a conventional snap fastener. Finally, in FIG. 13, coupled end 742 and coupled end 744 are provided with elongated cooperating hook and loop fastening strips 774 and 776. These elongated strips allow adjustment of the effective size of the band member, for example, when strap portions 718 and 720 are formed of a flexible but relatively non-elastic material.

Based upon the preceding description, one of ordinary skill in the art would appreciate that the earmuff assembly of the present invention would be comfortable to wear, compact for storage and lightweight. The construction is fashionable and, because of its sizing and light-weight, these earmuffs reduce damage to a hair style when worn. By having the pair of strap portions extend through the sleeve structures on opposite sides of each earmuff element, it is more difficult for wind to blow the earmuff elements away from the wearer's ears. The earmuff assembly can be adjusted for security and tightness around the wearer's head. And, the earmuff elements can be adjusted into a myriad of positions to accommodate various ear positions of various sized heads.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. An earmuff assembly adapted to be secured to a wearer's head in order to cover a wearer's ears, comprising:
   (a) a pair of earmuff elements each having a pair of spaced-apart sleeve structures disposed thereon;
   (b) a band member having opposite ends and including a pair of strap portions each having a length and each having a width, a first one of said strap portions being slidably received in a first one of said sleeve structures of each earmuff element and a second one of said strap portions being slidably received in a second one of said sleeve structures of each earmuff element whereby said earmuff elements may be selectively positioned along said band member between said strap portions; and
   (c) a joining means for interconnecting said opposite ends of said band member whereby said band member may be placed around and be retained by the head of a wearer with said earmuff elements oriented to cover the ears wherein the length of the first one of the strap portions extends along a first lateral side of each earmuff and the length of the second one of the strap portions extends along a second lateral side of each earmuff which is opposite to the first lateral side of each earmuff.

2. An earmuff assembly according to claim 1 wherein said band member is fabricated from an elastic material.

3. An earmuff assembly according to claim 1 wherein said opposite ends include an elastic material.

4. An earmuff assembly according to claim 1 wherein said pair of earmuff elements are fabricated from a pliable material.

5. An earmuff assembly according to claim 4 wherein said pliable material is selected from a group consisting of: fabric, leather, animal fur and imitation animal fur.

6. An earmuff assembly according to claim 1 wherein said pair of said earmuff elements are sized to cover the ears and shaped substantially rectangularly.

7. An earmuff assembly according to claim 6 wherein each of said earmuff elements includes a pair of sections of pliable material, said sections of pliable material sized to be superimposed over and connected to each other.

8. An earmuff assembly according to claim 7 wherein superimposing and connecting said sections of pliable material form said first and second sleeve structures.

9. An earmuff assembly according to claim 7 wherein one of said sections of pliable material is decorative.

10. An earmuff assembly according to claim 1 wherein said first and second sleeve structures of each earmuff element are disposed substantially parallel to one another.

11. An earmuff assembly according to claim 10 wherein each of said sleeve structures is a tubular member.

12. An earmuff assembly according to claim 10 wherein each of said sleeve structures includes a plurality of eyelets.

13. An earmuff assembly according to claim 1 wherein said joining means includes a matable pair of fastener elements whereby each of said fastener elements is adapted to connect to a respective one of said opposite ends.

14. An earmuff assembly according to claim 13 wherein said matable pair of fastener elements is selected from a group consisting of:
   a hook and loop fastener, a button and loop fastener, a snap fastener and a button and hole fastener.

15. An earmuff assembly according to claim 1 wherein said band member forms a continuous loop.

16. An earmuff assembly adapted to be secured to a wearer's head in order to cover the wearer's ears, comprising:
   (a) a pair of earmuff elements each having a pair of spaced-apart sleeve structures each disposed on opposite lateral sides thereof in a substantially parallel relationship and each of said earmuff elements sized to cover the wearer's ears and fabricated from a pliable material shaped substantially rectangularly;
   (b) a pair of elastic strap elements, each said strap element having a first end and an opposite second end and a central portion extending therebetween with said central portions each having a length, a first one of said central portions being slidably received in a first one of said sleeve structures of each earmuff element and a second one of said central portions being slidably received in a second one of said sleeve structures of each earmuff element wherein the length of first one of said central portions extends along a first lateral side of each earmuff element and the length of the second one of said central portions extends along a second lateral side of each earmuff element whereby said earmuff elements may be selectively positioned along said pair of strap elements and respective ones of said first ends and said second ends are connected to each other forming a pair of coupled ends thereby forming a continuous band member; and
   (c) a matable pair of fastening elements, a respective one of each fastening elements connected to a respective one of said coupled ends so that said coupled ends may be releasably connected to each other whereby said continuous band member may be placed around and be retained by the head of the wearer with said earmuff elements oriented to cover the ears.

17. An earmuff assembly according to claim 16 wherein each of said earmuff elements includes a pair of sections of pliable material having one of said sections of pliable material being decorative, said sections of pliable material sized to be superimposed over and connected to each other thereby forming said first and second sleeve structures.

18. An earmuff assembly according to claim 17 wherein each of said sleeve structures is a tubular member.

19. An earmuff assembly according to claim 17 wherein said pliable material is selected from a group consisting of: fabric, leather and animal fur and imitation animal fur.

20. An earmuff assembly according to claim 16 wherein each of said sleeve structures includes a plurality of eyelets.

21. An earmuff assembly according to claim 16 wherein said matable pair of fastening elements is selected from a group consisting of:
   a hook and loop fastener, a button and loop fastener, a snap fastener and a button and hole fastener.

22. An earmuff assembly adapted to be secured to a wearer's head in order to cover a wearer's ears, comprising:
   (a) a pair of earmuff elements each having a pair of spaced-apart sleeve structures disposed thereon in a substantially parallel relationship and each of said earmuff elements sized to cover a wearer's ears and fabricated from a pliable material shaped substantially rectangularly; and
   (b) an elastic continuous band member defined by a pair of strap portions interconnected by a pair of loop portions, said pair of strap portions extending through and between said earmuff elements and said pair of loop portions extending outwardly from respective ones of said earmuff elements, a first one of said strap portions being slidably received in a first one of said sleeve structures of each earmuff element and a second one of said strap portions being slidably received in a second one of said sleeve structures of each earmuff element whereby said earmuff elements may be selectively positioned along said pair of strap portions and said loop portions being interlinked to each other whereby said continuous band may be placed around and be retained by a head of a wearer with said earmuff elements oriented to cover the ears.

23. An earmuff assembly according to claim 22 wherein each of said earmuff elements includes a pair of sections of pliable material having one of said sections of pliable material being decorative, said sections of pliable material sized to be superimposed over and connected to each other thereby forming said first and second sleeve structures.

24. An earmuff assembly according to claim 22 wherein each of said sleeve structures is a tubular member.

25. An earmuff assembly according to claim 22 wherein each of said sleeve structures includes a plurality of eyelets.

26. An earmuff assembly according to claim 22 wherein said pliable material is selected from a group consisting of:
   fabric, leather and animal fur and imitation animal fur.

27. An earmuff assembly adapted to be secured to a head of a wearer in order to cover a wearer's ears, comprising:

(a) a pair of earmuff elements sized to cover the wearer's ears, each of said earmuff elements having a pair of sections of pliable material, said sections sized to be superimposed over and connected to one another thereby forming first and second sleeve structures spaced apart from one another and disposed on said earmuff elements in a substantially parallel relationship along respective longitudinal edges of said earmuff elements, each of said first and second sleeve structures extending substantially completely along an entire length of a respective longitudinal edge; and (b) an elastic continuous band member having a pair of tubular strap portions interconnected by a pair of loop portions, said pair of strap portions extending through and between said earmuff elements and a pair of loop portions extending outwardly from respective ones of said earmuff elements, a first one of said strap portions being slidably received in a first one of said sleeve structures of each earmuff element and a second one of said strap portions being slidably received in a second one of said sleeve structures of each earmuff element whereby said earmuff elements may be selectively positioned along said pair of strap portions and said loop portions being interlinked to each other whereby said continuous band may be placed around and be retained by the head of the wearer with said earmuff elements oriented to cover the wearer's ears.

\* \* \* \* \*